(12) United States Patent
Howland et al.

(10) Patent No.: US 7,799,563 B2
(45) Date of Patent: Sep. 21, 2010

(54) CARRIER FIBER ASSEMBLY FOR TISSUE STRUCTURES

(75) Inventors: Charles A. Howland, Temple, NH (US); Virginia Houston-Howland, Temple, NH (US); Jennifer K. White, Brookline, MA (US)

(73) Assignee: Warwick Mills, Inc., New Ipswich, NH (US)

( * ) Notice: Subject to any disclaimer, the term of this patent is extended or adjusted under 35 U.S.C. 154(b) by 1076 days.

(21) Appl. No.: 10/976,952

(22) Filed: Oct. 29, 2004

(65) Prior Publication Data

US 2005/0118716 A1 Jun. 2, 2005

Related U.S. Application Data

(60) Provisional application No. 60/515,373, filed on Oct. 29, 2003.

(51) Int. Cl.
*A61F 2/02* (2006.01)
(52) U.S. Cl. ............... 435/399; 623/23.76; 623/915
(58) Field of Classification Search .................. None
See application file for complete search history.

(56) References Cited

U.S. PATENT DOCUMENTS

| | | | | |
|---|---|---|---|---|
| 3,297,033 A | | 1/1967 | Schmitt et al. | |
| 3,316,557 A | * | 5/1967 | Liebig | 623/1.38 |
| 5,106,949 A | * | 4/1992 | Kemp et al. | 530/356 |
| 5,718,012 A | * | 2/1998 | Cavallaro | 8/94.11 |
| 5,733,337 A | | 3/1998 | Carr, Jr. et al. | |
| 5,911,942 A | * | 6/1999 | Fofonoff et al. | 264/444 |
| 6,485,723 B1 | | 11/2002 | Badylack et al. | |
| 6,638,312 B2 | | 10/2003 | Plouhar et al. | |
| 7,160,333 B2 | | 1/2007 | Plouhar et al. | |
| 2003/0028247 A1 | * | 2/2003 | Cali | 623/2.13 |

FOREIGN PATENT DOCUMENTS

WO    WO02/056800    *   7/2002

OTHER PUBLICATIONS

Stedman's Dictionary—pericardium (1 page).*
Mikos et al. (Journal of Biomedical Materials Research. 1993; 27: 183-189).*
Bordenave et al. Endothelium, 1999; 6(4): 267-275).*
Lewandrowski et al. (Journal of Biological Materials. 1996; 31: 365-372).*
Leong et al. (Composites: Part A. 2000; 31: 197-220).*
Stedman's Dictionary, 27th Ed. 2000. : pericardium (1 page).*
PCT International Search Report dated Apr. 6, 2006 of International Application No. PCT/US04/36231 filed Oct. 29, 2004.

* cited by examiner

*Primary Examiner*—Scott Long
(74) *Attorney, Agent, or Firm*—Vern Maine & Associates

(57) ABSTRACT

Methods and structures are disclosed where carrier fiber is used to enable the assembly of two and three dimensional structures of autologous tissue. Tissue is harvested from the donor, integrated with a carrier fiber, and assembled into complex forms rapidly. The structures can be tailored to the requirements of a specific medical procedure. The tissue is kept live and viable during extracorporeal assembly and the finished structure is emplaced in the donor's body. The use of a carrier fiber leader for pre-threading integration and assembly machines facilitates machine set up, drawing of the tissue into the process, and rapid integration and assembly of the multi-dimensional structures. Assembly can include providing tissue and fiber leaders extending from the structure for attaching the structure in place. The carrier fiber either is bio-absorbed as new tissue forms, or forms a bio-compatible substructure for the patient's native tissue.

13 Claims, 4 Drawing Sheets

CARRIER FIBER ASSEMBLY FOR TISSUE STRUCTURES

RELATED APPLICATIONS

This application claims the benefit of U.S. Provisional Applications No. 60/515,373, filed Oct. 29, 2003.

FIELD OF THE INVENTION

The invention relates to the use of carrier fiber for the assembly of autologous tissue structures for implantation in a patient's body, and more particularly to a process and machine for making two and three dimensional implantable structures of carrier fiber and autologous tissue.

BACKGROUND OF INVENTION

During conventional surgical procedures, a surgeon may use a patient's own tissue to repair or replace anatomical structures. These structures may be used with minimal modifications, such as when the saphenous vein is harvested from the leg and used as a conduit to supply blood flow to a coronary artery in cardiac bypass surgery. In other cases, the tissue can be significantly modified, and then used. The pericardium (the membranous sac around the heart) has been harvested, chemically treated, and then reconfigured to make heart valve leaflets for valve repair or replacement.

Constructing three-dimensional biological structures ("bio-structures") in the operating room is difficult. Surgeons can't spend too long making complex functional structures from an individual's tissues, and there are limited tools available. The patient's tissues are limited in quantity, difficult to work with, and often not accessible or permissible to remove. These constraints restrict the sophistication of the current surgical procedures which involve manipulating a patient's own tissues ("autologous tissues") during surgery. These limitations inhibit the clinician from envisioning new potential therapies and surgical strategies based upon complex modification of tissues in the operating room.

Prior strategies to overcome these difficulties include 1) pre-forming complex anatomical structures from synthetic materials prior to the surgery, 2) using non-synthetic tissues with inherent structure harvested from a range of sources, and 3) using specialized instrumentation for constructing complex biological structures in the operating room.

Textile technology has been used in medicine providing synthetic implants for patients. Weaves, knits, braids, and meshes of synthetic materials have been used in strips, sheets, and tubular configurations. As examples, woven or knitted polyester sewing rings are used in prosthetic heart valves and woven "Surgicel"™ cellulose or "Iodoform"™ gauze in sheets or strips are used for epitaxis and wound packing. Other examples include knitted Dacron (polyester) tubular conduits used in peripheral vascular surgery and braided stainless steel "Wallstent"™ cylinders for stenting the respiratory and gastrointestinal tract. Knitted polypropylene mesh sheets have found application to reduce tension in hernia repair. In these examples, textile processing is used to impose structure and promote tissue encapsulation of the synthetic (heart valve ring), trap cells to enhance blood clotting or absorb fluids (Surgicel or Iodoform), provide a three-dimensional configuration for fluid flow or stenting (vascular graft or Wallstent), or alter biomechanics, e.g. tensile strength or elasticity (hernia mesh).

In general, the application of textile technology (e.g. weaving, knitting, braiding) to a base material increases the implant's surface area, enlarges the interspaces between fibers, and increases the mass of material in the structure. In using synthetics as a base material, this processing also increases the mass of the foreign body which in many applications, imposes an increase risk of infection and immunological incompatibility. In addition, these structures are not living tissues and have no ability to repair, regenerate, or grow at the cellular, tissue or organ level.

Another strategy has been to use tissues from various sources to form the desired bio-structures in patients. In certain instances, using tissues as a base material for implants imparts intrinsic three-dimensional structure, reduces the foreign body reaction, or retains the tissues living capabilities of cellular repair, regeneration, and growth. Tissue implants fall into three broad categories which include xenografts (from another species), homografts (from the same species), and autografts (from the same individual). Examples are glutaldehyde-fixed porcine pericardium heart valves (xenograft), kidney transplant from a cadaver (homograft), and skin grafts in burn patients (autograft). The general characteristics of xenografts, homografts, and autografts have unique properties as compared to native tissue. In general, tissue derived from a xenograft is less pliable and supple and incapable of cellular repair, regeneration, or growth characteristics since they are rendered nonviable due to chemical treatments used to reduce their immunogenicity. Homografts have more pliability than xenografts, but are non-living and scare in availability. Autologous tissues retain pliability and living capabilities but require careful non-traumatic handling and time-sensitive harvesting, reconstruction, and implantation to preserve these characteristics. The majority of xenografts, homografts, and autografts tissues have been used as implants without the application of textile technology to form the desired structures.

For the most part, surgeons rely on conventional hand-held surgical instrumentations for reconstructing tissues by incising, shaping, and suturing tissues into three-dimensional shapes. An example of the use of more specialized instrumentation is a split-thickness skin grafting technique during which the surgeon uses a dermatome to harvest a thin layer of patient's skin and a specialized slitting tool to make an array of incisions in the skin, allowing the graft to be expand into a mesh configuration with a larger surface area. Another prior use of intra-op instrumentation designed to create a three-dimensional shape is the use of specialized tissue cutting templates, jigs, and forms to create tri-leaflet heart valves from a planar sheet of the patient's pericardium. There are few examples of these tools for specialized procedures and they are not widely applied in surgery. The majority of surgery is performed using a standard set of hand-held instruments.

SUMMARY OF THE INVENTION

In this invention, carrier fiber is used to facilitate the assembly of two and three dimensional structures with autologous tissue. Autologous tissue is harvested from the donor and assembled into complex forms rapidly. The tissue is kept live and viable during extracorporeal assembly and is replaced in the donors body. The use of carrier fiber facilitates this rapid assembly of the two and three dimensional structures. The autologous tissue is modified into thin long sections and is integrated with the carrier fiber. Carrier fiber of various types are used to facilitate the assembly process. The use of twisting, spinning, weaving, knitting, and braiding assembly processes to integrate the carrier fiber and the autologous tissue strips is made practical for assembly into structures by using long pre-threaded carrier yarn leaders for machine set up, in order to draw the autologous tissue into the assembly process when ready. In this way, the limited quantity of autologous tissue is not wasted in the set up and thread-up of the assembly equipment. The finished autologous structures allow for complete healing in the patients body. The carrier fiber of the tissue/fiber composite structure is either bio-absorbed or forms a bio-compatible substructure for the patient's native tissue as healing progresses.

It is therefore an objective of the invention to provide a process by which autologous or other tissue that has been harvested or otherwise produced, can be processed, and assembled into two and three dimensional structures suitable for medical implantation as a tissue-based scaffold to support the growth or regrowth of native tissue.

It is a further objective to provide a machine by which such a process may be conducted.

DESCRIPTION OF PREFERRED EMBODIMENT

Figure 1:
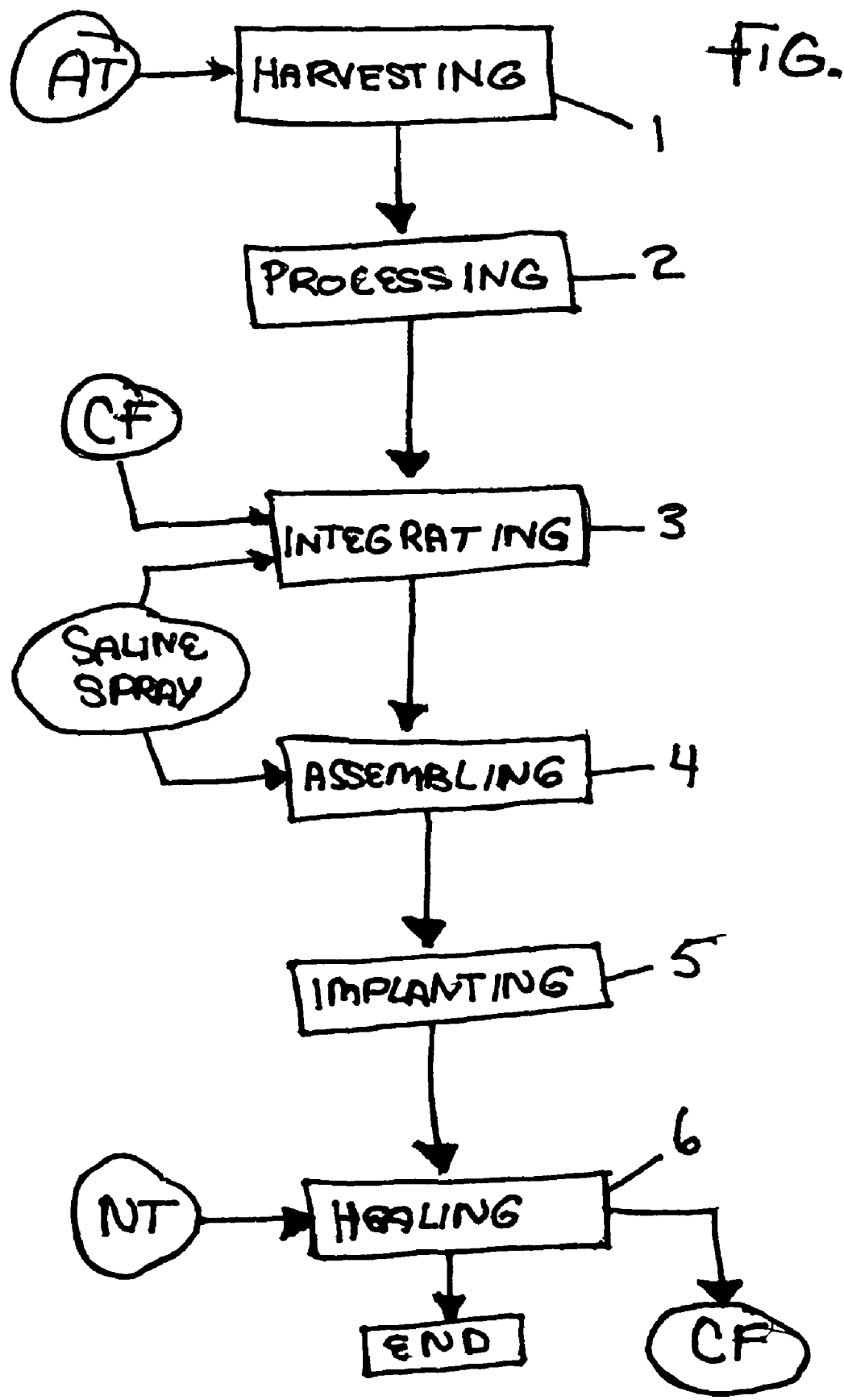
FIG. 1 is a simplified flow chart of a preferred embodiment of the invention.

The invention is susceptible of many embodiments. What is explained here are preferred embodiments and best mode for practicing the invention, and should be construed as illustrative and not limiting of the invention.

While preferred embodiments presume the tissue to be autologous tissue being used for assembly into useful fiber/tissue structures for surgical implantation in the donor's own body; the description and claims extend to the use of any living or synthetic tissue or tissue precursor in the process of the invention, whether naturally occurring or cultivated in an alternate fashion, whether harvested from the recipient or from another natural or cultivated source.

Selection Of Carrier Fiber

The preferred carrier fiber or yarn (CF) system is of small denier in the 10 to 300 range. In many situations, it is desirable for the carrier fiber to be absorbable in the body. Poly Glycolic Acid (PGA) and Poly Lactic Acid (PLA fibers has been used extensively in suture yarns and have well known bio-absorption characteristics. The PGA/LGA fiber also have tensile and modulus characteristics that are biocompatible based on its experience base from use in surgical sutures.

In addition to the use of bio-absorbable fiber, the use of fixed animal fiber is also an option. Also materials such as those based on various collagen types have application to the invention. The relative value of carrier fiber types is dependent on the interaction with healing mechanisms in the body. In addition to the type of stresses, the time frame for healing will suggest the optimum carrier fiber type for use in a structure. In some case the use of synthetic fibers like polyester may be indicated.

Autologous Tissue Processing

The harvesting of Autologous Tissue (AT) and manufacturing of AT yarn or tape (ATY) is surgical in nature. Pericardium or other appropriate membranes are removed from the patient's body and mounted on a frame. In a preferred method, a spiral ruled cutter and press form a narrow tape from the harvested membrane. For the manufacture of small vessels, the ATY has to be small, preferably 0.005-0.025 inches in width. Other larger structures may be able to use ATY as large as 0.1 inches in width. The appropriate autologous membranes may not have a thickness compatible with these dimensions and can be skived, planed, slit or microtomed to meet a desired dimension. This process also offers the surgeon the control options for the type of tissue to be used to form the ATY. In most cases the membrane and tissues that can be harvested have a multi-layer structure. It may be desirable to use only some of these layers and not use others in the formation of ATY. Other cutting or fiber formation methods such a straight-line slitting, laser cutting, water jet cutting, or helical slitting are all candidate methods for formation of ATY. The ATY need not be monofilament in nature; it can be multifilament or it can be multifilament with twist as in a staple fiber formation, which will be readily understood by those in the textile arts.

Yarn sizes and vessel wall thickness must be related. For very small structures, such as 1 or 2 mm diameter veins, the wall thickness must be equally thin. In this case the available autologous tissue membrane may require not only thin sectioning into tapes or strips but also reduction in thickness. This processing can be done both before and after the initial sectioning has been done and can include both mechanical rolling or drawing and cutting or skiving techniques. The imperfections in the ATY in very thin sections result in higher breakage and reduce the average length of undivided material. However with the use of fine CF these shorter ATY sections are supported and carried through the assembly process.

Equipment Setup

The use of carrier fibers allows the fabrication equipment to be setup and all the elements to be threaded and ready for the surgical session. The use of live autologous tissue requires that the assembly process be rapid and reliable. The threading of the equipment with ATY would not only consume time during the procedure but would also require large amount of ATY for threading and start up. The use of carrier yarn leaders allows all the thread up and tension control devices to be initialized with the bare carrier yarn CF leaders, and the ATY used almost exclusively for the formation of the finished structure. In addition to speed and utilization advantages, the carrier fiber provides an improved cover factor in the ATY fabric and helps reduce the porosity of the structure. The term "cover" or "cover factor" and various other terms and phrases of the textile arts used through this specification are defined and/or clarified by reference to other Charles A. Howland patents including U.S. Pat. Nos. 5,564,264; 5,837,623; and 5,976,996, and also to such industry references as the Dictionary of Fiber and Textile Technology, copyright 1999 KoSa, ISBN 0-9670071-0-0.

Autologous Tissue and Healing

The use of ATY fabrics and structures allows the healing process in the body to take over and remake the structure. During this healing process the carrier fiber fills in as a tension bearing threadline or matrix, for defects in the ATY and the assembly process. There will be splices, terminations and incomplete coverage of the ATY portion of the structural fabric initially. Before the healing process has corrected these small imperfections, the carrier fiber provides both redundant structure and improved surface area coverage.

Figure 2:
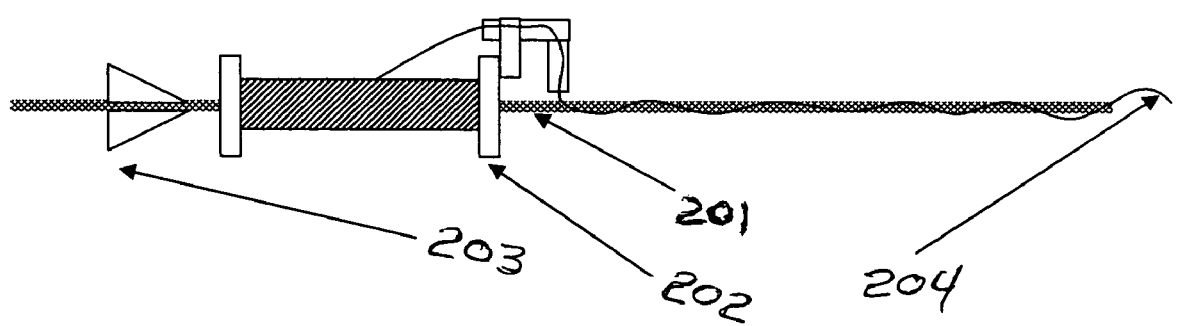
FIG. 2 is a diagrammatic illustration of a ply twisting operation for integrating tissue yarn with a carrier fiber.

Integration of CF to ATY with the carrier yarns is the first step in the assembly process. Ply twisting, hitch loops, serving, wrapping or braiding, terms understood in the textile arts, are all useful in integrating the ATY with the CF. Each method is outlined below. Referring to FIG. 2, in the ply twisting case, a preferred approach makes use of short lengths to be processed, and feeds the ATY 201 from a fixed position, with the bobbin of CF 202 moving around the ATY material. In some cases, a rotating hollow clamp 203 is used to guide the continuous CF and the free end of the ATY. The clamp turns and provides the ply twist for the CF/ATY pair 204.

The use of multiple CF yarns is useful to help support thin or fragile ATY. After twisting, the free ends of the ATY are released from the rotating and fixed clamp. They are then knotted or coated to prevent untwisting. The integrated section of ATY and CF is then be advanced into the assembly section of the apparatus. It is preferred to use a balanced twist (s versus z) in the CF singles yarn to prevent liveliness or torque in the ply structure. A ply twist between 1 and 30 turns per inch is typical to integrate CF with ATY. Twisting has the advantage that the process is simple and a hundred or more clamp-type twisting units take up little space, facilitating the parallel integration of the CF and ATY. The multi-up assembly process, well understood to those skilled in the textile arts, is also desirable as it avoids the requirement to move integrated thread lines from the CF/ATY integration step to the assembly step. In the case of weaving or other assembly modes where multiple ends are required, this parallel process can save time in the procedure.

A second configuration of CF integrated with ATY is where the CF forms a clove hitch over the free end of the ATY. Additional hitch or loop fastening of CF to ATY is used along the ATY length to integrate the two yarns, the fastening points being spaced as often as necessary to provide adequate thread line behavior.

A serving or winding configuration uses a hollow bobbin and feeds the ATY through the hollow core. In general a CF yarn is paired with the ATY in the core feed to support the ATY and reduce the lengths required. In this process the wrap count of the CF is selected to meet the required thread line behavior. The number of CF wraps per inch should not be excessive as a very high CF cover would reduce the available surface area of the ATY and hence the healing performance of the integrated finished CF/ATY fiber.

Figure 3:
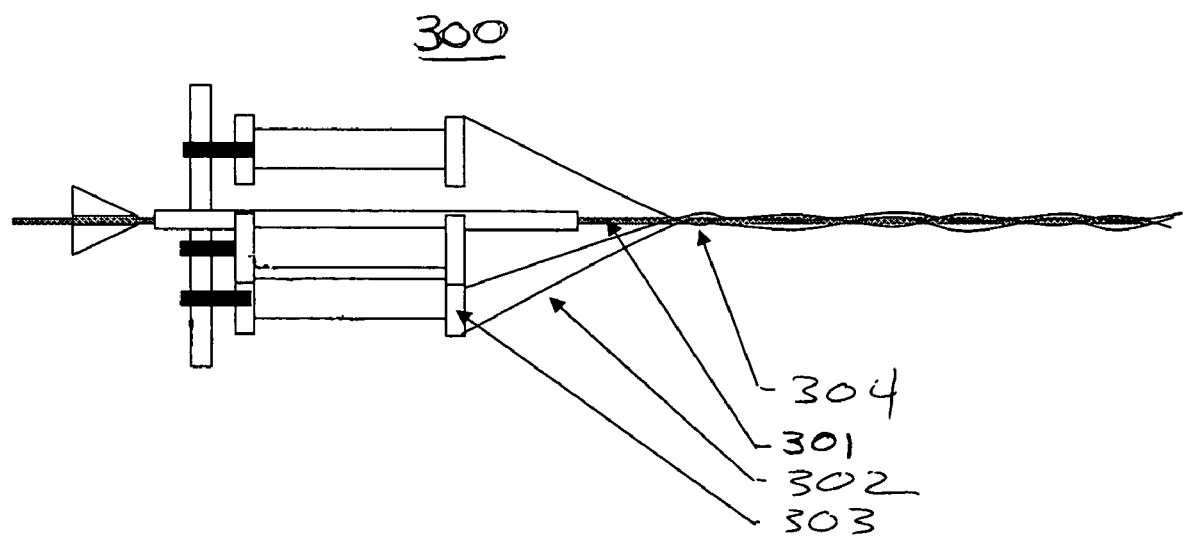
FIG. 3 is a diagrammatic illustration of a braiding operation for integrating tissue yarn with a carrier fiber.

Referring to FIG. 3, in the braiding process and configuration, the CF 302 is set up on the three bobbins 303 in the braiding unit 300 and ATY 301 is feed as a core to the braid at braid point 304. This method provides very low ATY tension in the integration process and is useful for handling very short sections of ATY. The braiding process is desirable when integrating CF and ATY for knitting as the braiding process can be run in parallel with the knitting or weaving filling insertion of the structure. The braiding complexity makes it less attractive for use as a warp component of assembly where more thread lines are required. Core braid insertion for CF/ATY can be readily automated.

Assembly of useful tissue fabrics and structures using the integrated CF/ATY may be accomplished in several ways; as described in the following examples.

EXAMPLE #1

Weaving of Tubular ATY/CF Structures Oriented in the Fill Direction

Figure 4:
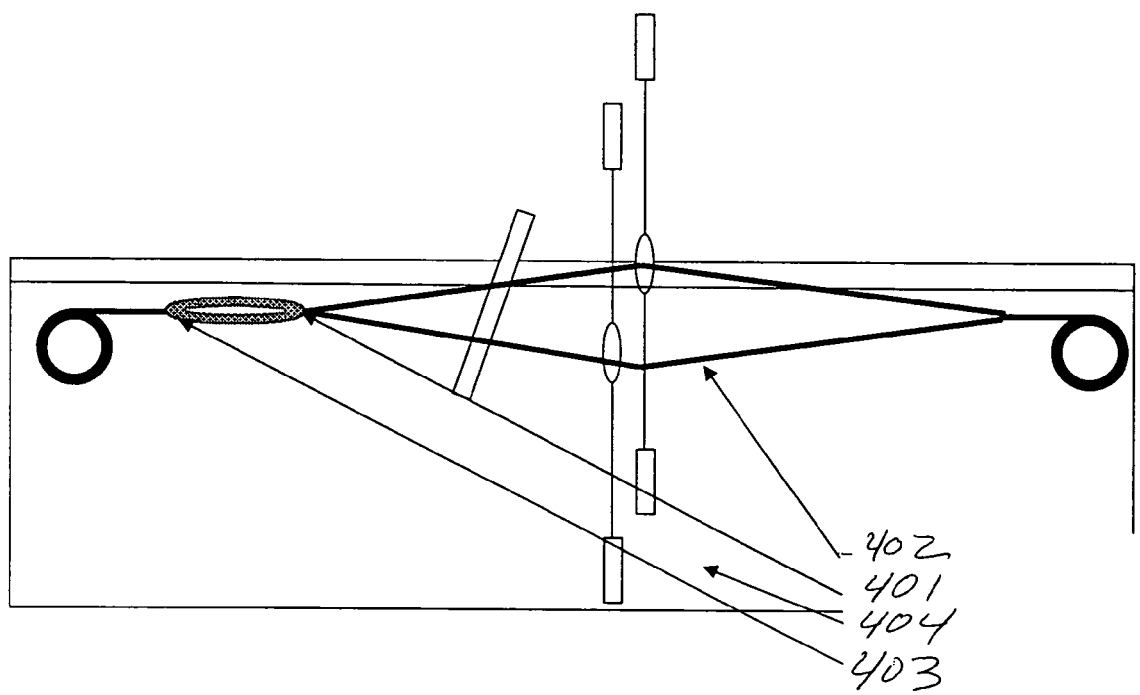
FIG. 4 is a diagrammatic illustration of weaving a fabric tube with tissue yarn in the fill and carrier fiber in the warp.

The first example of an ATY/CF scaffold or structure and process of the invention is of weaving ATY/CF fabric tubes oriented in the fill direction. For this example, cylindrical tubes are fabricated to various lengths and diameters. The use of a weaving process is preferred because it allows separate selection of the thread line density and type in the axial and circumferential directions. Narrow width weaving equipment of a few inches is preferred. Needle or rapier insertion is best for the filling insertion mechanism. Referring to FIG. 4, the major modification of the heddle/reed insertion section 400 is the use of an aqueous saline bath 404 to preserve the viability of live tissue. Tissue yarn ATY 401 is used in filling, and carrier fiber CF 402 is used in warp. The weave design uses the filling oriented tube method. The key advantage of this system over warp oriented tubes is the ease with which the tube diameter can be modified by simply changing the number of filling insertions in the double layer section. Tube diameter variation is necessary to match the donor's native vessels and is not known with precision except at the time of performing the associated medical procedure.

For this set up, the preferred warp feed would be from a single end creel for the CF warp. As described, the clamp-type twisting or knotting integration methods are preferred as inline or parallel parts of the creel thread lines. This process creates a set of ATY/CF warp yarns. The normally very limited amount of ATY requires that the ATY/CF yarns each have a length close to the total length required for the structure being formed. The rest of the threaded length for the assembly equipment can be provided by the CF only, as an ATY/CF yarn leader. After the required number of CF/ATY thread lines have been integrated, the integrated sections are moved into the assembly zone in the fabric forming equipment. In the example of weaving equipment, this would move the CF/ATY yarns into the fell zone and just at the location for next insertion to fall on integrated CF/ATY sections. In the case of knitting or braiding equipment, a similar advance into the assembly zone starts the next part of those processes.

In the case of woven structures, the filling direction yarns can be different than the warp yarns. In some cases, the CF yarn need only be used in one of the machine directions. In the general case, there are integrated CF/ATY lines or yarns in both directions. This provides additional options for configuring the effective cover of the ATY related healing and face-side related symmetry and asymmetry options for medically healing and tissue presentation, the means for achieving which will be understood by those in the textile arts.

In the case of the warp yarn, there are a number of options for integration. The ATY can be knotted, served with a second CF tread line, twisted into a ply with the CF or braided into an integrated unit. In the case of the filling yarn, the degree of mechanical abrasion in weaving is very low and the required filling feed tension is also very low. This allows for using a very limited degree of integration or amount of CF to ATY, and even the use of no CF material and only ATY, in the filling direction when desirable.

In the example of a CF/ATY fabric tube or vessel assembly with weaving, the selected filling type, CF, ATY, or CF/ATY, is inserted into a warp pattern that links all the warp fiber units. The optimal weave pattern in this Closed Tape Zone (CTZ) is a tight plain weave with weave cover in the range of 50-80%. The number of insertions will depend on the width of the CTZ and the inter-fiber friction of the total system. In the preferred case, small CF material is woven to create a tight CTZ to prevent any structural problems such as the loss of crossing points after removal for use on the assembly fixture. As with a fringe or any fabric edge, the CTZ may be terminated with knots to further prevent loss of crossing points.

After the completion of the CTZ, the tube section (TS) of the assembly is formed. In this step of the assembly process the warp fiber is controlled with the hettles to create two sheets in the formation zone. Typically half the warp fiber is formed into an upper sheet and the other half is formed into the lower sheet. The TS formation continues until the required tube diameter is formed. The actual resulting TS diameter can be tested with a mandrel by slacking off the warp tension at this point in the process. When the TS is long enough then the second CTZ can be formed and this allows for a closed tube.

At this point the formed tube can be removed from the assembly unit and the CTZ and ends can be finished as required to prepare the ATY/CF structure or scaffold for insertion into the patient's body.

EXAMPLE #2

Weaving of Tubular ATY/CF Structures Oriented in the Warp Direction

The second example of an ATY/CF scaffold or structure and process according to the invention is the weaving of a warp oriented tube. In this example, shuttle type weaving is preferred and the formation is of a two-ply fabric with woven selvedges. This follows the techniques for fly shuttle weaving, which are well understood in the textile arts. The filling yarn must be wound on a shuttle bobbin and the shuttle moves for each filling insertion. In this method the tube diameter must be pre-defined as the warp end-count and the reed size in use will define the tube circumference. The key advantage of this method is the elimination of the CTZ (closed tape zone) at the two edges of the tube. With fly shuttle weaving, woven selvedges avoid the requirement of a CTZ. With these exceptions to the first example fill direction tube process, all the other weaving related process specifications apply. Combined and/or bifurcated structures based on this and the other assembly techniques described herein are also possible.

EXAMPLE #3

Braiding of ATY/CF Structures

The third example of an ATY/CF scaffold or structure and process according to the invention is of braiding methods and braided structures useful for the assembly of small vessel scaffolds. The CF is integrated with the ATY as described and is wound on bobbins. The section of integrated CF/ATY is moved forward into the braiding zone and the structure is fabricated using the required number of braided ends for the tube size required. The method may be preferred for the elasticity intrinsic to the braid and rapid change in tube diameter, mirroring the recipient's vessel variation. It should be noted that fiber orientation in such structures is limited and cover in larger vessel sizes requires very complicated equipment.

EXAMPLE #4

Knitting of ATY/CF Structures

The fourth example of an ATY/CF scaffold or structure and assembly process according to the invention is of knitting methods and knitted structures. The use of circular knitting and other complex knitting methods known in the textile arts are used for larger tubular and bifurcated structures. As the gage of the knitting machines is limited, the fineness of knitted structures is less appropriate in small structures. However the knitting process has the advantage of only requiring a few yarn ends for processing. The integration of the ATY and the CF can be accomplished in-line with the knitting process. The use of knit structures is desirable when very compliant structures are required. However cover and porosity characteristics in knitted structures are not ideal for liquid tight requirements and such ATY/CF scaffolds or structures may require post processing to address these issues.

Environmental Conditions in the Assembly Process

The integration and assembly process is accomplished at low temperature and under saline spray or saline immersion. The time required for CF/ATY formation, integration, assembly and post processing defines the environmental requirements. The longer the process time needed, the lower the temperatures required, the more critical the saline formulations are to maintaining the viability of the ATY tissue.

Crossing Point Design

At the level of fabric design, the options for the integration of the CF and ATY materials are numerous. A key criteria in this step or design is keeping the cover factor and available surface areas of ATY in a ratio that facilitates complete healing. In some cases the ATY materials will need to be nearly continuous on the surface of the structure. This is accomplished in one way by having much smaller carrier fibers relative to the size of the ATY material. A preferred pattern in this case would cross the CF on the ATY with respect to machine directions and pack the ATY in the pattern to provide optimal cover. In other situations where healing mechanisms allow for incomplete ATY coverage, CF can be used to complete the surface of the structure. Patterns where only some of the fibers contain ATY in either or both directions are within the scope of the invention. It is expected that symmetrical face patterns will be used in some applications. However in cases where the inside and outside of a vessel have differential healing characteristics, the ratio of ATY and CF can be asymmetrical as in twill or sateen designs. Those skilled in the textile arts will readily understand such variations.

Post Processing and Re-introduction

When there is excessive porosity in the assembled part, this may be addressed either by mechanical compaction of the surface as with calendering or by coating with various surgical dips. As in the case of synthetic grafts, the use of albumin or blood is useful in closing any fine porosity in a newly assembled structure.

In many situations, the use of CF, ATY, or CF/ATY fibers in the terminations of the structure can be used as the suture for the emplacement of the structure in the patient's body. This method avoids the need to penetrate the assembled structure with a separate suture. As the assembled structure is manufactured to fit the reassembly site in the donor, the suturing is made in a preferred geometry to accommodate the planned placement. This preserves the integrity of the structure and promotes rapid healing.

Referring now to FIG. 1, the six fundamental steps of the invention are illustrated. At step 1, autologous tissue AT, or any tissue, is harvested from its source in a non-destructive manner. At step 2, the tissue is processed by any of the means described above into an ATY or autologous tissue yarn format suitable for the process that follows. At step 3, as described above, a medically suitable carrier fiber CF is integrated with the ATY to form a workable composite yarn of CF and ATY. As illustrated in FIG. 1, preferred embodiments use a saline spray, and low temperature environment, to promote the longevity of the tissue material during this and subsequent steps. At step 4, again as aptly described above, CF/ATY yarn, and optionally unintegrated CF and ATY, are assembled into a tissue and fiber fabric structure of the desired geometry and balance of physical properties of the tissue and fiber, suitable for a specific medical implantation requirement.

The integration and assembly steps of the process of FIG. 1 draw heavily on the art, practice, and machines of the textile industry in novel and heretofore unobvious ways to advance this aspect of the medical arts. The invention extends further to the use of carrier fiber leaders for machine set up to conserve tissue and accelerate the process, then for drawing of the tissue into the integrating step and of the carrier fiber and tissue composite into the assembly process. As shown, a saline spray and other efforts may be used to maintain the viability of the tissue during integration and assembly steps until the step 5 implantation is accomplished. In healing step 6, new tissue NT builds on the AT tissue, gradually replacing the carrier fiber CF and fleshing out the full form of the structure as the CF is slowly absorbed.

The invention has many possible embodiments and variations. For example, there is a process for repair of a tissue-based body structure in a patient using the steps: harvesting autologous tissue from a donor; processing the autologous tissue into autologous tissue yarn; integrating the autologous tissue yarn with a carrier fiber into a fiber/tissue composite yarn; using a leader of carrier fiber for drawing the composite yarn into an assembly process; assembling by the assembly process a fiber and autologous tissue body structure; and implanting the structure in the patient.

The processing step may include reducing the autologous tissue into strips of 0.005 to 0.1 inches in width. The integrating step may use at least one technique from among the group of techniques consisting of ply twisting, hitch loops, serving, wrapping, braiding, and entanglement. The assembly process may include any of: weaving a tubular tissue and fiber structure oriented in the fill direction; weaving a tubular tissue and fiber structure oriented in the warp direction; braiding a tissue and fiber structure; knitting a tissue and fiber structure; or other manual or machine construction of structures by use of yarns and fibers.

The integrating step and/or the assembling steps may include applying lower than ambient temperature and a saline solution to the autologous tissue. The assembly process may include weaving a tissue and fiber fabric on a machine where the autologous tissue yarn is run in one machine direction and the carrier fiber is run in the other machine direction. The assembly process may include compacting the walls of the structure and/or coating the structure for reducing porosity.

The assembly process may include terminating the fabrication of the structure leaving extended lengths of yarn suitable for suturing the structure into place, where the yarns are any or all of carrier fiber, tissue yarn, or the composite fiber/tissue yarn.

Another example of the invention is a produce of the process, a structure formed by the process. The structure may incorporate a fabric constructed of autologous tissue yarn and carrier fiber and containing crossing points formed by any of weaving, knitting, braiding or entanglement techniques, or other techniques.

As another example of the invention, there is a process for making a tissue-based body structure consisting of the basic steps: processing body tissue into tissue yarn; integrating the tissue yarn with a carrier fiber into a fiber/tissue composite yarn; using a leader of the carrier fiber for drawing the composite yarn into an assembly process; and assembling by the assembly process a fiber and tissue structure. This example may employ the other variations and options described above, as well as products of the process of this example and its variations.

Yet another example of the invention is simply a structure made from a fabric consisting of autologous tissue yarn and carrier fiber, where the tissue yarn consists of strips of tissue between 0.005 and 0.1 inches in width. And a further simple example is a structure made from a fabric consisting of a composite yarn consisting of comprising autologous tissue yarn and carrier fiber, again where the autologous tissue yarn consists of strips of autologous tissue between 0.005 and 0.1 inches in width.

Other and various examples and variations of the invention will be evident from the abstract, description, figures, and following claims.

We claim:

1. A continuous process for making a tissue and fiber fabric structure during a surgical procedure on a live body, and implanting the structure in the live body, the process comprising the steps of:
    harvesting live autologous tissue membrane from the live body during the surgical procedure;
    forming the live autologous tissue membrane into strips of live tissue yarn of 0.005 to 0.1 inches or 0.13 to 2.6 mm in width;
    integrating said live tissue yarn with a carrier fiber into a composite yarn of live tissue and fiber;
    using a leader of said carrier fiber for drawing said composite yarn into an assembly process;
    assembling by said assembly process a fabric structure of fiber and live tissue; and
    implanting said tissue and fiber fabric structure in the live body, said strips of live tissue yarn remaining sufficiently viable to integrate with each other and with surrounding tissue in the live body according to a healing process.

2. The process according to claim 1, said step of integrating comprising at least one from among the group of techniques consisting of ply twisting, hitch loops, serving, wrapping, braiding, and entanglement.

3. The process according to claim 1, said assembly process comprising the step:
    weaving a tubular structure comprising live tissue and fiber.

4. The process according to claim 1, said assembly process comprising the step:
    braiding a structure comprising live tissue and fiber.

5. The process according to claim 1, said assembly process comprising the step:
    knitting a structure comprising live tissue and fiber.

6. The process according to claim 3, said step of weaving comprising the step:
    weaving a fabric comprising live tissue and fiber wherein said live tissue yarn is run in one machine direction and said carrier fiber yarn is run in the other machine direction.

7. The process according to claim 1, said assembly process comprising
    terminating the assembling of said structure with lengths of yarn suitable for suturing said structure into place in said patient, wherein said lengths of yarn comprise at least one from among the group of yarns consisting of said fiber yarn, said live tissue yarn, and said composite yarn.

8. A structure formed by the process of claim 1.

9. A tissue and fiber fabric structure comprising:
    a fabric comprising an assembly of live autologous tissue yarn and carrier fiber yarn, said tissue yarn comprising live strips of tissue membrane between 0.005 and 0.1 inches or 0.13 to 2.6 mm in width, said strips having been cut from live, viable tissue membrane harvested from a live body during a surgical procedure and combined with said carrier fiber into said assembly, said live strips of tissue membrane remaining sufficiently viable to integrate with each other and with surrounding tissue according to a healing process if the structure is re-implanted into the live body during the surgical procedure.

10. A tissue and fiber fabric structure comprising:
a fabric, said fabric comprising a composite yarn, said composite yarn comprising carrier fiber and at least one strip of live autologous tissue membrane between 0.005 and 0.1 inches or 0.13 to 2.6 mm in width, said strips having been cut from live, viable tissue membrane harvested from a live body during a surgical procedure and combined with said carrier fiber into said composite yarn, and said yarn constructed into said fabric, said strips remaining sufficiently viable to integrate with each other and with surrounding tissue according to a healing process if the structure is re-implanted into the live body during the surgical procedure.

11. The process according to claim 1, further comprising, during at least one of the steps of forming, integrating, using, and assembling, the step of applying an aqueous saline solution to the live autologous tissue membrane, the aqueous saline solution being formulated so as to support viability of the live autologous tissue membrane during the process.

12. The process according to claim 11, wherein applying an aqueous saline solution includes at least one of submerging the live autologous tissue in a bath of the aqueous solution and spraying the live autologous tissue with the aqueous saline solution.

13. The process according to claim 1, further comprising, during at least one of the steps of forming, integrating, using, and assembling, the step of maintaining the live autologous tissue membrane at a temperature below ambient that is consistent with supporting viability of the live autologous tissue membrane.

* * * * *